United States Patent
Saget et al.

(10) Patent No.: US 10,463,435 B2
(45) Date of Patent: Nov. 5, 2019

(54) SURGICAL INSTRUMENT POSITIONING SYSTEM, APPARATUS AND METHOD OF USE AS A NONINVASIVE ANATOMICAL REFERENCE

(71) Applicant: OrthoGrid Systems, S.A.R.L., Salt Lake City, UT (US)

(72) Inventors: Edouard Saget, Salt Lake City, UT (US); Richard Boddington, Salt Lake City, UT (US); Taylor Fry, Dallas, TX (US)

(73) Assignee: Orthogrid Systems, Inc, Salt Lake City, UT (US)

( * ) Notice: Subject to any disclaimer, the term of this patent is extended or adjusted under 35 U.S.C. 154(b) by 0 days.

(21) Appl. No.: 16/312,405

(22) PCT Filed: Jun. 30, 2017

(86) PCT No.: PCT/US2017/040392
§ 371 (c)(1),
(2) Date: Dec. 21, 2018

(87) PCT Pub. No.: WO2018/006026
PCT Pub. Date: Jan. 4, 2018

(65) Prior Publication Data
US 2019/0231442 A1    Aug. 1, 2019

Related U.S. Application Data

(60) Provisional application No. 62/357,214, filed on Jun. 30, 2016.

(51) Int. Cl.
*A61B 34/20* (2016.01)
*A61F 2/46* (2006.01)
(Continued)

(52) U.S. Cl.
CPC .......... *A61B 34/20* (2016.02); *A61B 17/7074* (2013.01); *A61F 2/46* (2013.01);
(Continued)

(58) Field of Classification Search
CPC ..... A61B 34/20; A61B 17/70; A61B 17/7074; A61F 2/46
See application file for complete search history.

(56) References Cited

U.S. PATENT DOCUMENTS 5,880,976 A    3/1999  DiGioia et al.
7,559,931 B2   7/2009  Stone
(Continued)

FOREIGN PATENT DOCUMENTS

CA    2889146 A1    5/2014

OTHER PUBLICATIONS

Hsiu-Hsia Lin et al, Three-Dimensional Computer-assisted surgical simulation an intraoperative navigation in Orthognathic Surgery: A Literature Review, J. of the Formosan Med. Assoc. 2015 114, 300-307 K Taiwan).

(Continued)

*Primary Examiner* — Christopher J Beccia
(74) *Attorney, Agent, or Firm* — Veritay Group IP PLLC; Susan B. Fentress

(57) ABSTRACT

The subject of this invention is a surgical instrument positioning system, method and apparatus, using an anatomical reference plane registered in a non-invasive manner and a method of intra-operative use of this instrument for joint replacements, spine, trauma fracture reductions and deformity correction and implant placement/alignment.

5 Claims, 10 Drawing Sheets

(51) Int. Cl.
*A61B 17/70* (2006.01)
*A61B 17/56* (2006.01)
*A61B 90/00* (2016.01)

(52) U.S. Cl.
CPC . *A61B 2017/564* (2013.01); *A61B 2090/3764* (2016.02); *A61B 2090/3966* (2016.02); *A61B 2090/3983* (2016.02)

(56) References Cited

U.S. PATENT DOCUMENTS

| | | |
|---|---|---|
| 8,118,815 B2 | 2/2012 | Walt |
| 8,241,296 B2 | 8/2012 | Wasielewski |
| 8,526,700 B2 | 9/2013 | Isaacs |
| 8,718,346 B2 | 5/2014 | Isaacs et al. |
| 8,792,704 B2 | 7/2014 | Isaacs |
| 8,961,526 B2 | 2/2015 | Burroughs |
| 8,974,467 B2 | 3/2015 | Stone |
| 8,998,910 B2 | 4/2015 | Borja et al. |
| 9,119,572 B2 | 9/2015 | Gorek et al. |
| 9,125,678 B2 | 9/2015 | Lye |
| 9,138,319 B2 | 9/2015 | Fanson et al. |
| 9,271,756 B2 | 3/2016 | Walt et al. |
| 9,295,555 B2 | 3/2016 | Caylor |
| 2009/0226060 A1 | 9/2009 | Gering et al. |
| 2009/0285366 A1 | 11/2009 | Essenreiter et al. |
| 2011/0071529 A1 | 3/2011 | Carson |
| 2011/0152676 A1 | 6/2011 | Groszmann et al. |
| 2014/0276871 A1 | 9/2014 | Sherman et al. |
| 2014/0303631 A1 | 10/2014 | Thornberry |
| 2015/0142372 A1 | 5/2015 | Singh |
| 2015/0289992 A1 | 10/2015 | Anglin et al. |

OTHER PUBLICATIONS

PCT Preliminary Report on Patentability PCT/US17/40392.

SURGICAL INSTRUMENT POSITIONING SYSTEM, APPARATUS AND METHOD OF USE AS A NONINVASIVE ANATOMICAL REFERENCE

CROSS REFERENCE TO RELATED APPLICATIONS

This application is a § 371 National Stage Application of PCT/US17/40392 application filed Jun. 30, 2017 and U.S. provisional patent application Ser. No. 62/357,214 filed Jun. 30, 2016, under 35 U.S.C. § 111(a) (hereby specifically incorporated herein by reference).

STATEMENT REGARDING FEDERALLY SPONSORED RESEARCH OR DEVELOPMENT

None.

REFERENCE TO SEQUENCE LISTING, A TABLE FOR A COMPUTER PROGRAM LISTING, COMPACT DISC APPENDIX

None.

FIELD OF THE INVENTION

The subject of this invention is a surgical instrument positioning system, an apparatus using an anatomical reference plane registered in a non-invasive manner and a method of intra-operative use of this instrument for joint replacements, spine, trauma fracture reductions and deformity correction and implant placement/alignment.

BACKGROUND OF THE INVENTION

Many of the radiographic parameters essential to total hip arthroplasty (THA) component performance, such as wear and stability, can be assessed intraoperatively with fluoroscopy. However, even with intraoperative fluoroscopic guidance, the placement of an implant or the reduction of a bone fragment may still not be as close as desired by the user. For example, mal-positioning of the acetabular component during hip arthroplasty can lead to problems. For the acetabular implant to be inserted in the proper position relative to the pelvis during hip arthroplasty requires that the user know the position of the patient's pelvis during surgery. Unfortunately, the position of the patient's pelvis varies widely during surgery and from patient to patient. During trauma surgery, proper fracture management, especially in the case of an intra articular fracture, requires a user to reduce the bone fragment optimally with respect to the original anatomy to: provide the joint the best chance to rehabilitate properly, minimize further long-term damage and, if possible, to regain its normal function. Unfortunately, in a fracture scenario, the original anatomical position of these bone fragments has been compromised and their natural relationship with the correct anatomy is uncertain and requires the user to use his/her best judgment to promote a successful repair and subsequent positive outcome.

Various devices are known to reduce mal-positioning of these surgical components. For example, a transverse acetabular ligament has been suggested as a qualitative marker of the orientation of the acetabulum. (Archbold H A, et al. The Transverse Acetabular Ligament; an Aid to Orientation of the Acetabular Component During Primary Total Hip Replacement: A Preliminary Study of 200 Cases Investigating Postoperative Stability, J Bone Joint Surg BR. 2006 July; 88(7):883-7). However, it has been suggested that the acetabulum may be deteriorated due to arthritis. Others have proposed using a tripod device that uses the anatomy of the ipsilateral hemi pelvis as the guide to position the prosthetic acetabular component. U.S. Patent Publication Number 20090306679. This instrument has three points. The first leg is positioned in the posterior inferior acetabulum, a second leg is positioned in the anterior superior iliac spine and a third leg is positioned on the ileum of the subject. U.S. Patent Publication Number 20090306679. Regarding fracture fixation, or a correction of a deformity or malunion, various devices have also been suggested to support proper reconstruction or reduction of bone fragments. For example, a distal radius volar fixation plate has been suggested to act as an invasive, intraoperative quantitative supporting buttress to fix and provide a reference to the user to help realign the broken bony anatomy.

Most surgical instruments positioning systems are navigated one or several anatomical reference planes that are initially registered in relative position to temporarily implanted fixed markers tracked by a computer system via various methods, such as IR, EMF, etc. The precision of these systems helps users to position instruments and implants with the expectation to improve patient outcomes. The invasiveness of these trackers is minimal but has been documented to lead to fractures and other complications, such as insertion site pain. In addition, the set up is lengthy and adds considerable time to the surgery. Other systems which attempt to register a non-invasive reference plane are extrapolating the plane from a non-anatomical reference, such as the horizontal plane of an operating table. The accuracy of such system has not proved any additional benefit in surgical instrument and implant position. A new way to identify the reference plane in a non-invasive and time effective manner based on known and proven anatomical markers is needed.

SUMMARY OF THE INVENTION

The present subject matter includes a method for intra-operatively navigating a surgical device. The steps of this method include: overlaying a dimensioned pattern over an image of a patient's anatomy; defining a coronal plane of the patient anatomy with reference to the dimensioned pattern; defining a sagittal plane of the patient's anatomy with reference to the dimensioned pattern; extrapolating a third axis from the coronal plane and the sagittal plane to form a 3-dimensional reference plane; obtaining intraoperative positional data for a surgical device with reference to the 3-dimensional reference plane; communicating the intraoperative positioning data of the surgical device to a user, and intra-operatively navigating the surgical device with reference to the positioning data.

The present subject matter further includes the step of using a primary alignment device, wherein the primary alignment device is made of a movable dimensioned grid having a plurality of dimensioned radiopaque patterns corresponding to a plurality of surgical variables, the primary alignment device being adjusted to define the coronal plane and sagittal plane of the patient's anatomy.

The present subject matter further includes the step of attaching a surgical device to a secondary alignment device, wherein the secondary alignment device is made of a guide to provide an angle between the surgical device and the secondary alignment device, and aligning the secondary alignment device with the primary alignment device, with reference to a defined coronal plane of the patient anatomy and a defined sagittal plane of the patient's anatomy.

In the present method, the intraoperative positional data for a surgical device is obtained from a plurality of reference plane axis trackers positioned on the surgical device; the intraoperative positional data for the surgical device is obtained from a plurality of reference plane axis trackers positioned on the primary alignment device and the intraoperative positional data for the surgical device is obtained from a plurality of reference plane axis trackers positioned on the secondary alignment device.

The present subject matter further includes a surgical navigation system made of: a non-transitory computer-readable storage medium encoded with computer-readable instructions which form the application software, a signal receiver communicatively coupled to at least one processor, wherein one of the at least one processors is programmed to receive a first digital image of a patient's anatomy; receive a digital image of a patient's anatomy adjusted for correct anatomical rotation with reference to a dimensioned pattern overlaid on the image of a patient's anatomy, the dimensioned pattern positioned on a primary alignment device; receive reference plane axis trackers data from a surgical device; receive reference plane axis trackers data from a primary alignment device; and compute a three-dimensional position of the surgical device, wherein one of the at least one processors is communicatively coupled to a display providing visual feedback regarding the three-dimensional position of the surgical device with respect to an anatomical feature.

BRIEF DESCRIPTION OF THE SEVERAL VIEWS OF THE DRAWING

The invention description refers to the accompanying drawings.

DETAILED DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for describing embodiments by way of example only and is not intended to be limiting of the claimed invention. Also, as used in the specification including the appended claims, the singular forms "a," "an," and "the" include the plural, and reference to a numerical value includes at least that value, unless the context clearly dictates otherwise. Ranges may be expressed herein as from "about" or "approximately" one value and/or to "about" or "approximately" another value. When such a range is expressed, another embodiment includes from the one value and/or to the other value. Similarly, when values are expressed as approximations, by use of the antecedent "about," it will be understood that the value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions and are not restrictive of the invention as claimed. Unless defined otherwise, all technical and scientific terms used herein have the same meaning as commonly understood by one of ordinary skill in the art to which this invention belongs.

Figure 1:
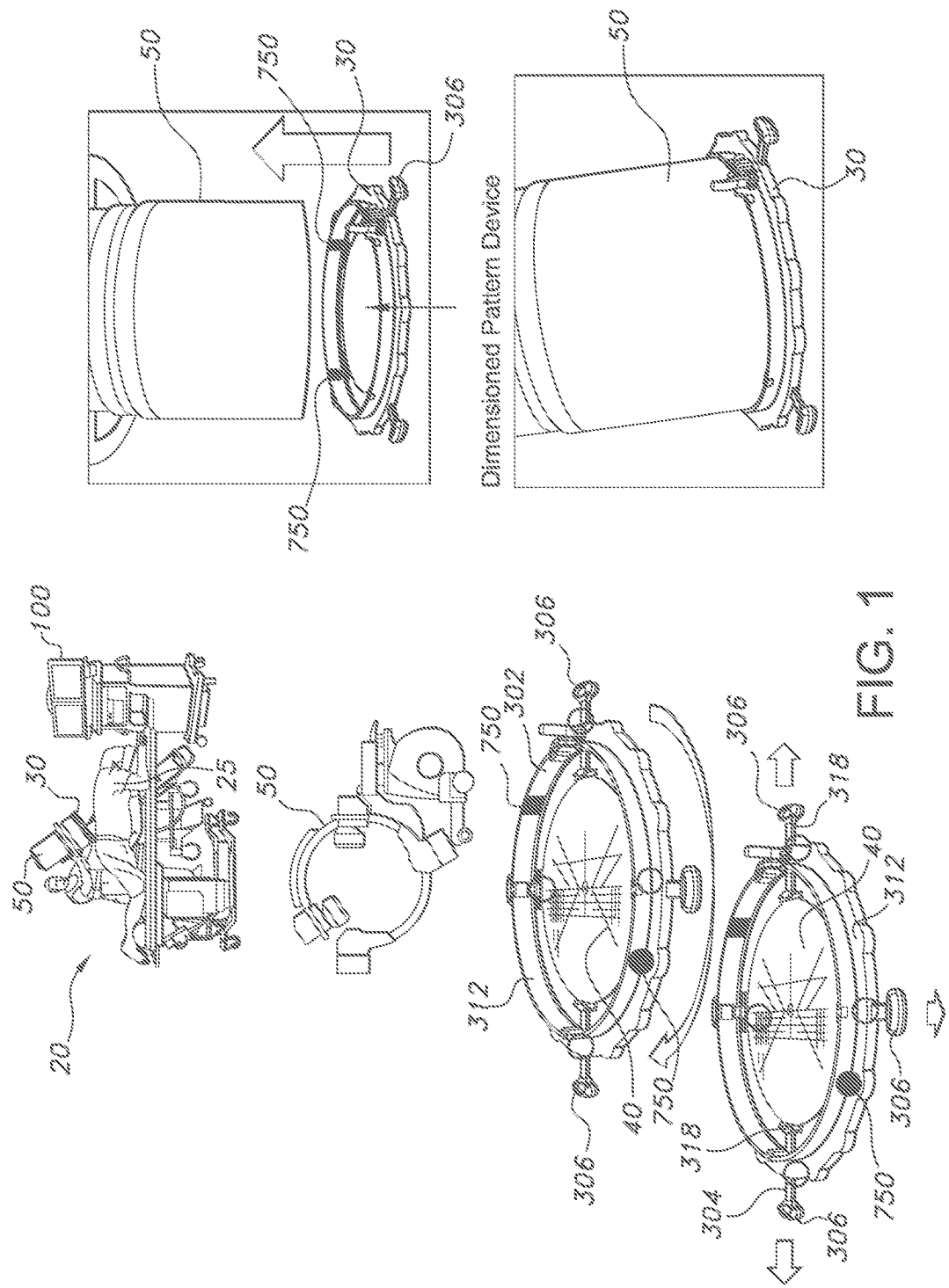
FIG. 1 is an illustrative embodiment of a surgical instrument positioning system and an apparatus using an anatomical reference plane registered in a non-invasive manner.
Figure 2:
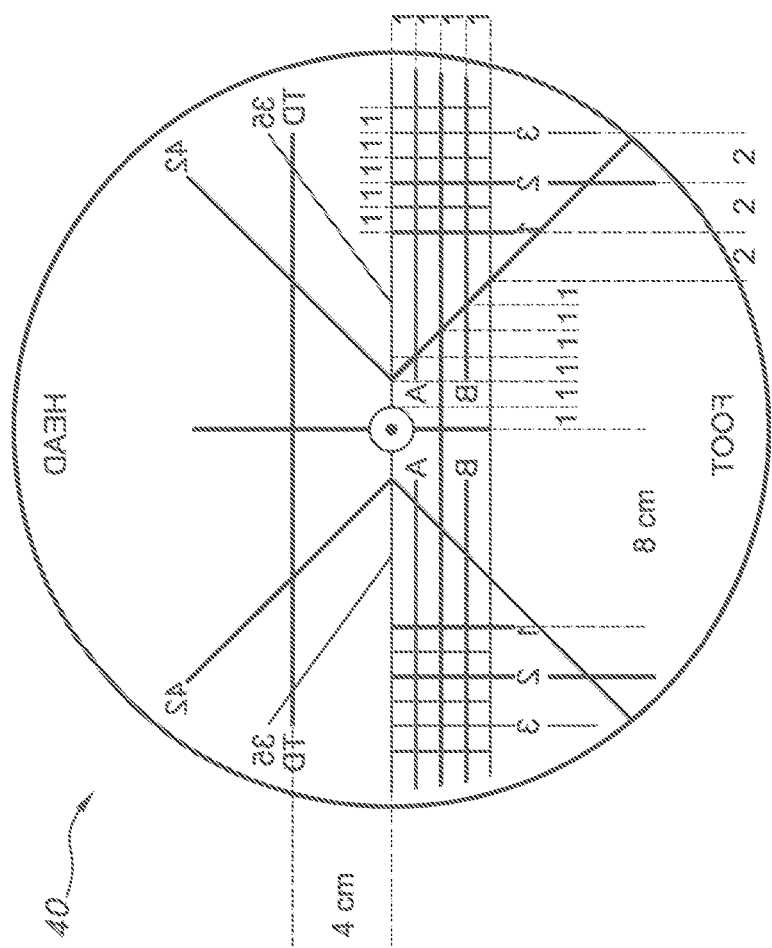
FIG. 2 is an illustrative embodiment of a dimensioned radiopaque pattern.

Now referring to FIGS. 1-2, a surgical instrument positioning system 20 is shown. The surgical instrument positioning system 20 includes a primary alignment device 30 with a dimensioned radiopaque pattern 40 attached to or generated by an imaging device 50. The primary alignment device 30 is attached to an imaging device 50 and is electronically connected to a computing system 100. In operation, the surgical instrument positioning system 20 provides guidance to a user 27 in positioning or tracking a surgical device, such a surgical instrument 80 (FIG. 8), during intra-operative use of this instrument on a patient 25 for joint replacements, spine, trauma fracture reductions and deformity correction and implant placement/alignment. The primary alignment device 30 has a plurality of reference plane axis trackers 750 positioned on the device.

A dimensioned radiopaque pattern 40 is attached to an image intensifier of the imaging device 50. In another embodiment, the dimensioned radiopaque pattern 40 is generated by the application software. In one embodiment, the image is in the DICOM image format. See U.S. Pat. Nos. 8,611,504, and 9,610,134 (hereby specially incorporated by reference in their entity).

Figure 10:
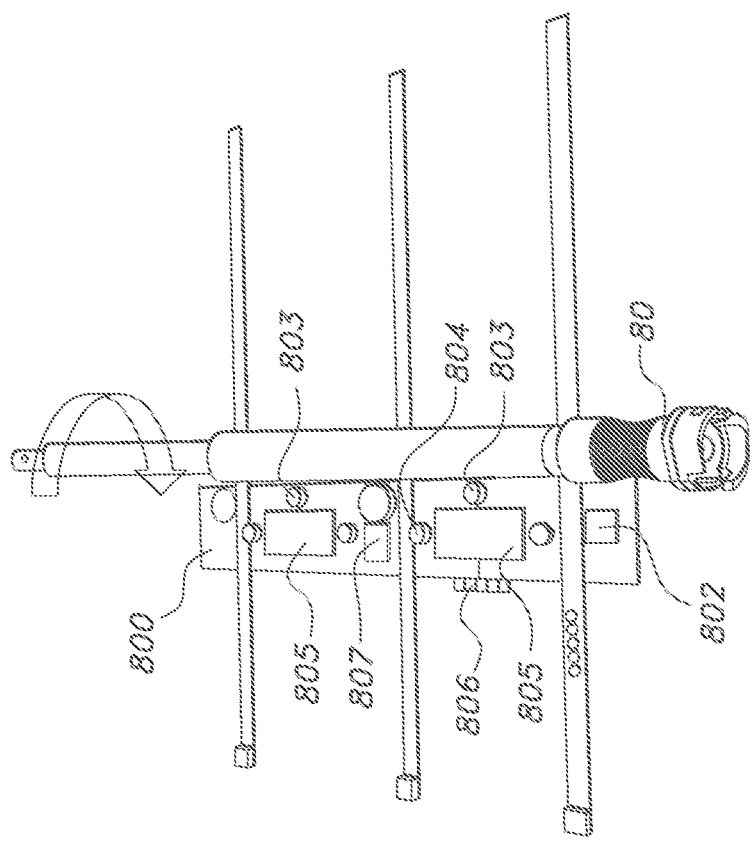
FIG. 10 is. a schematic diagram of showing an alternate embodiment of the alignment device for a surgical instrument.

The primary alignment device 30 is made of a movable dimensioned grid having a plurality of dimensioned radiopaque patterns corresponding to a plurality of surgical variables. More specifically, the primary alignment device 30 is made of an inner circular section 302 having a plurality of radial fixturing grips 304 each with an enlarged end 306. The inner circular section 302 of the primary alignment device 30 has a plurality of dimensioned lines relating to surgical variables. In one embodiment, the lines are radioopaque. The primary alignment device 30 is made of a retaining member, that is formed of a pressing plate 318 and rotating ring 312. The rotating ring 312 has a plurality of slots each are sized to retain an enlarged end 306 having a plurality of radial fixturing grips 304 to allow planar movement of the alignment device 30, in several degrees of freedom. The rotating ring 312 is affixed to the C-arm head of an imaging device 50. The primary alignment device 30 has a plurality of reference plane axis trackers 750 positioned on the device. The plurality of reference plane axis trackers 750 allow accurate guidance of the Z plane and 3D space in conjunction with the use of a dimensioned grid 40. A second level guide, shown in FIG. 10, is provided to allow the setting to keep a surgical instrument 80 such as a tool at a desired tilt angle as well as rotation for tools where rotation is of concern (such as a bone saw).

In a method for intra-operatively navigating a surgical device, the specifically spaced and quantified vertical elements of a known dimensioned pattern 40, are overlaid over an image of the patient's anatomy, such as an AP Pelvis, in the center of a 2D image. The first step of the process involves the overlay of the dimensioned radiopaque pattern 40 over an image of the patient's anatomy 25. This allows a user to adjust the imaging device 50 or the position of the patient 25 to adequately and accurately represent a patient specific rotated AP Pelvis view. This defines the coronal plane of the pelvis or the z axis.

The second step of the process involves: defining the coronal plane of the patient anatomy 25. The specifically spaced and quantified horizontal elements of a dimensioned pattern, are overlaid on a AP Pelvis in the center of a 2D image. This allows a user to adjust the imaging device 50 or the patient position to adequately and accurately represent a patient 25 specific tilt in the AP Pelvis image. This defines the sagittal plane of the pelvis or the Y axis.

The next step of the process involves: extrapolating the third axis from the 2D anatomical reference plane once two axes have been identified, the surface of the imaging device 50 becomes the parallel transposition of these two axes into space. As a result, the remaining axis can be identified as the perpendicular to both these axes. At which point, a 3-dimensional reference plane, aligned accurately with the anatomy is determined. The fourth step of the process involves: extrapolating the third axis, which forms a 3-dimensional reference plane.

The next step of the process involves tracking and/or navigating the surgical instrument. If the dimensioned radiopaque pattern 30 continues to track the anatomical landmarks via imaging analysis software tools, such as auto segmentation and auto tracking. Additionally, trackers positioned both on the primary alignment device 30 and on the surgical device, such as an instrument 80 allow a user to navigate, live and position in space, a surgical instrument in either one or multiple planes. The next step of the process involves: obtaining positioning data to track and or navigate of surgical instrument.

The next step of the process involves visually or digitally communicating/displaying positioning information to a user 27. The positioning data can be communicated to an outside display unit, either analog or digital, including but not limited to: a computer monitor, mobile device or portable augmented, virtual reality or heads-up type display. The sixth step of the process involves communicating the positioning data to the user and intra-operatively navigating the surgical device with reference to the positioning data.

Figure 3:
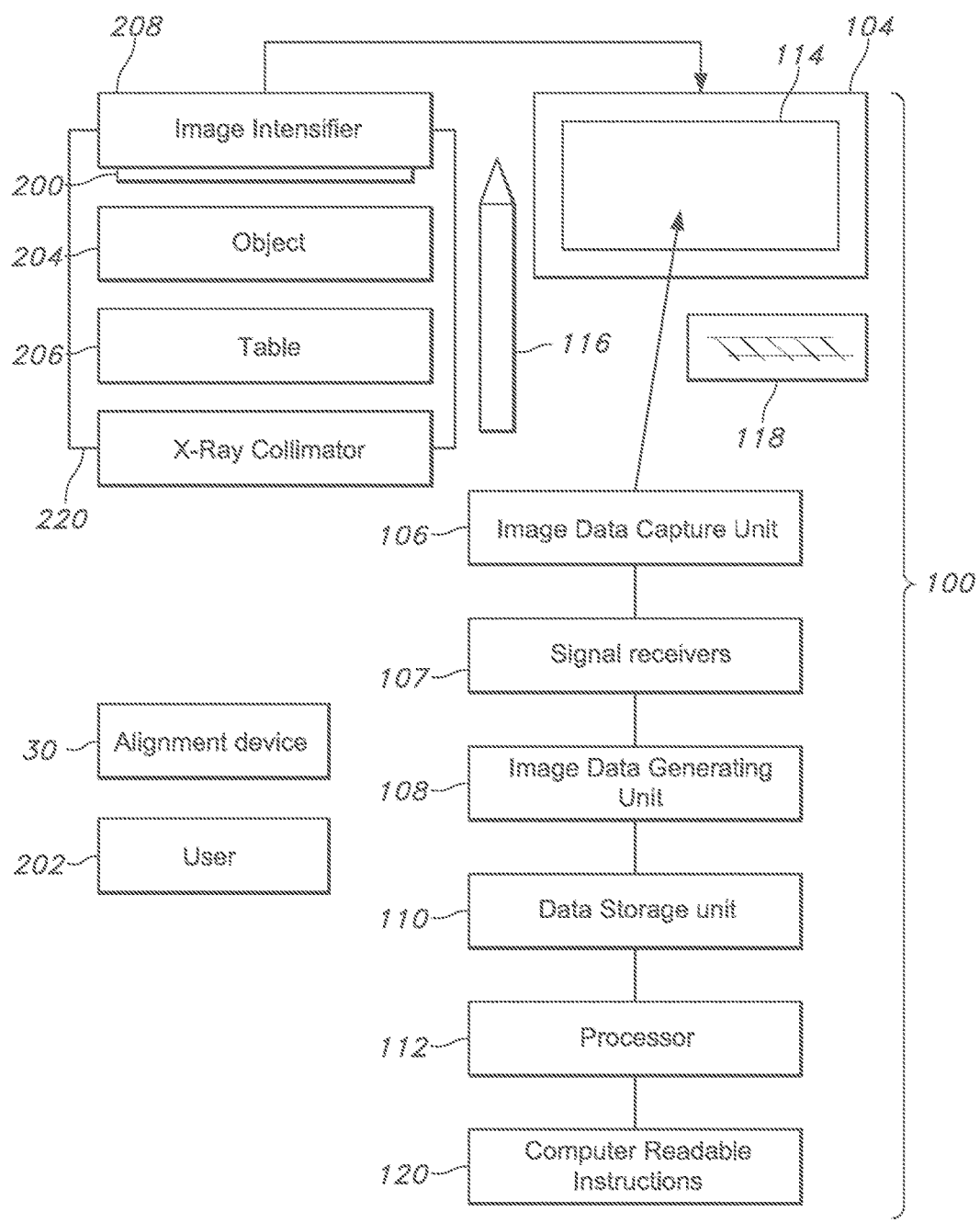
FIG. 3 is a block diagram showing the system of the present invention.

Now referring to FIG. 3, this method is accomplished using a computing system 100. This computing system includes: a computer workstation 104. The computer workstation 104 is made of: an image data capture unit 106; a plurality of signal receivers 107, an image data generating unit 108; a non-transitory computer-readable image data storage medium 110; a processor 112 communicatively coupled to at least: the image data capture unit 106 a plurality of signal receivers 107 and an image data generating unit 108; and computer-readable instructions 120. The non-transitory computer-readable storage medium 110 is encoded with computer-readable instructions, which form the application software 120. The computer workstation 104 also includes an input device 118, such as, a key board, and a display 114, such as a monitor. The non-transitory computer-readable storage medium 110 is coupled to the processor 112 and is configured to store data unique to each surgery and to provide an anatomical model for each type of surgery. The storage medium 110 can save imaging data from current and past sessions.

The computer system 100 can optionally include a motion-tracking device 116. In an exemplary embodiment, an image capture unit 106; an image data generating unit 108 includes measurements and data that can be acquired and displayed on AR/Holo lenses, glasses, or a heads-up display. The computer workstation 104 is electronically connected to an imaging system 220, such as a C-arm and flat plate. An object, such as a patient 25, is positioned on a table 206 within the imaging system 220.

Figure 4:
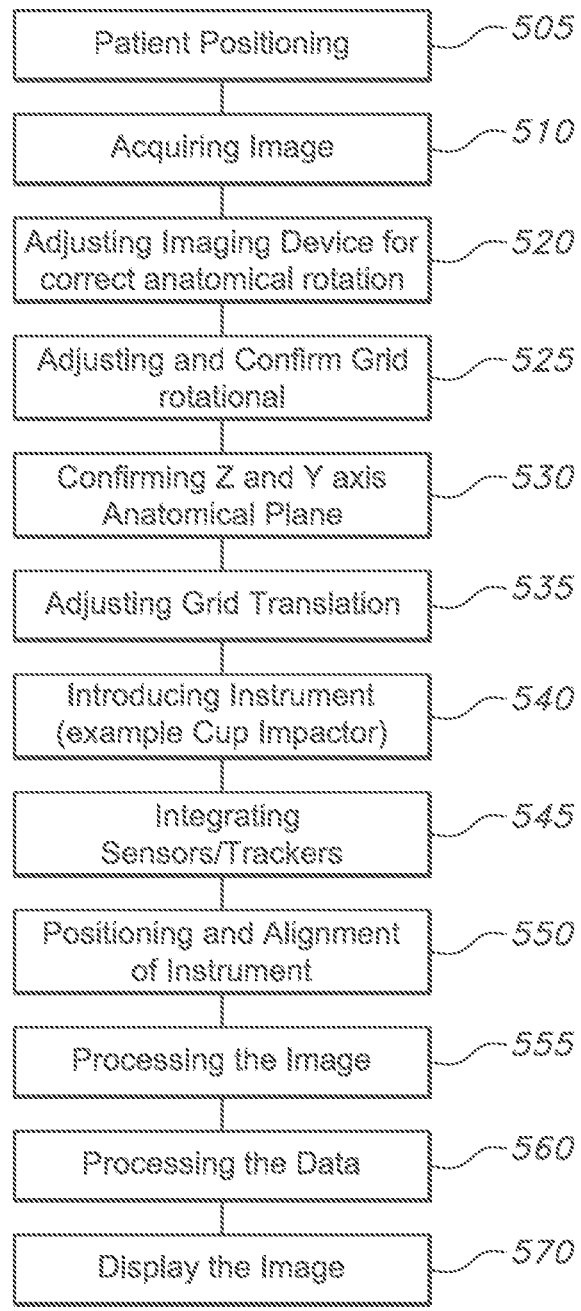
FIG. 4 is a flow chart showing an overview of the method of the present invention.
Figure 5:
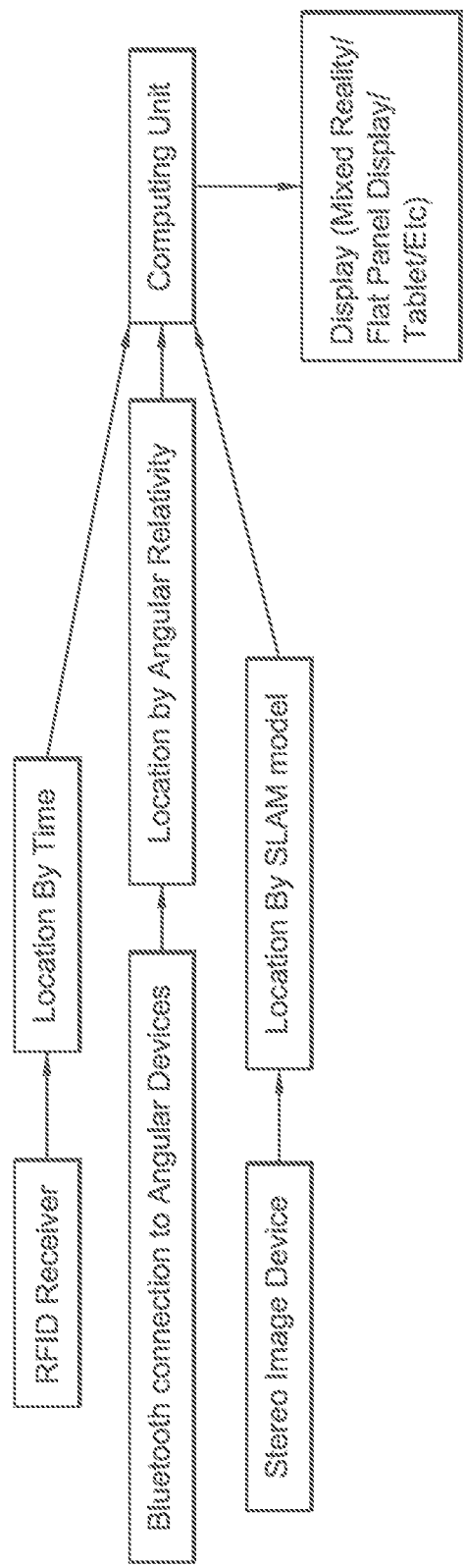
FIG. 5 is a diagram showing the sensor configurations.
Figure 6:
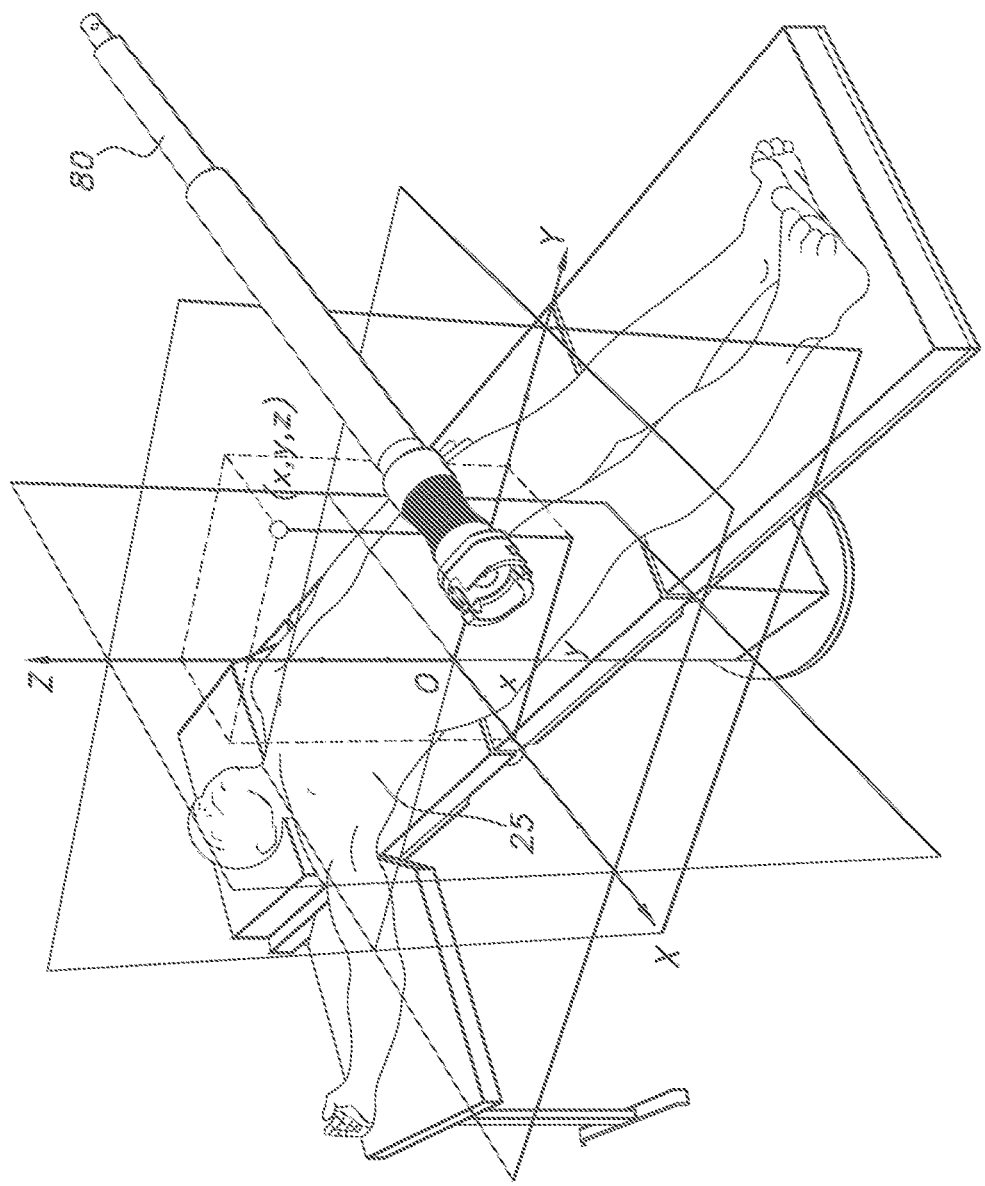
FIG. 6 is a schematic diagram of showing the three-dimensional reference plane of this invention.

Now referring to FIGS. 4-6, the process of this invention begins with the step of positioning the patient 505, acquiring an image 510; adjusting the imaging device for correct for anatomical rotation 520; adjusting and confirming grid rotational orientation; confirming the Z and the Y anatomical plane 530, adjusting grid translation 535; introducing a surgical device, such as an instrument or a tool 540; integrating sensors/trackers 545; positioning and alignment of the surgical device, such as an instrument 550; processing the image 555, processing the data 560 and displaying the image 570.

The process involves tracking and/or navigating the surgical instrument. If the dimensioned radiopaque pattern 30 continues to track the anatomical landmarks via imaging analysis software tools, such as auto segmentation and auto tracking. Additionally, trackers positioned both on the primary alignment device 30 and on the surgical device, such as an instrument 80 allow a user to navigate, live and position in space, a surgical instrument in either one or multiple planes To accomplish tracking and/or navigating the surgical instrument a plurality of reference plane axis trackers are positioned on the surgical device 80 and on the primary alignment device 30 and optionally on a secondary alignment device 800 (FIG. 10). These reference plane axis trackers can include: at least one passive RFID receiver affixed to the surgical device 80. The passive RFID receiver is used with an active reader to read a time pulse to test for distance and to fix location by time. The reader is electronically connected to the computing system 100. The reader measures signal strength to determined position.

In one illustrative embodiment, multiple readers can be used each having a known distance from each other so that they can pin-point a location with greater accuracy. This data re the location by time of the surgical device 80 is provided to the computing system 100. Simultaneously, a BLUETOOTH connection between a sensor on the surgical device 80 and a sensor on the primary alignment device 30 compare angles and wirelessly send this data to the computing system 100. This provides the location of the instrument by determination of the location by angular relativity. These angular sensors measure a tool angle to the C-Arm angle wirelessly to compare the two.

In an alternate embodiment, a gyroscope can be positioned on the primary alignment device 30. In this situation, the primary alignment 30 device tells the computer its orientation and the attachment with sensors on the surgical device 80 such as a tool reports its data to the computer as well. Also, a stereo image device can be placed on the surgical device 80 and the primary alignment device 30 to provide the location by the SLAM model. The stereo image uses a SLAM model to judge distances. This data is transmitted to the computing system 100. This positional data is averaged based on weight of accuracy and importance to reduce error. The user is then able to know his or her location and his or her destination, based on previous studies of landmarks and templates stored in memory of the computing system 100.

EXAMPLE 1

Figure 7:
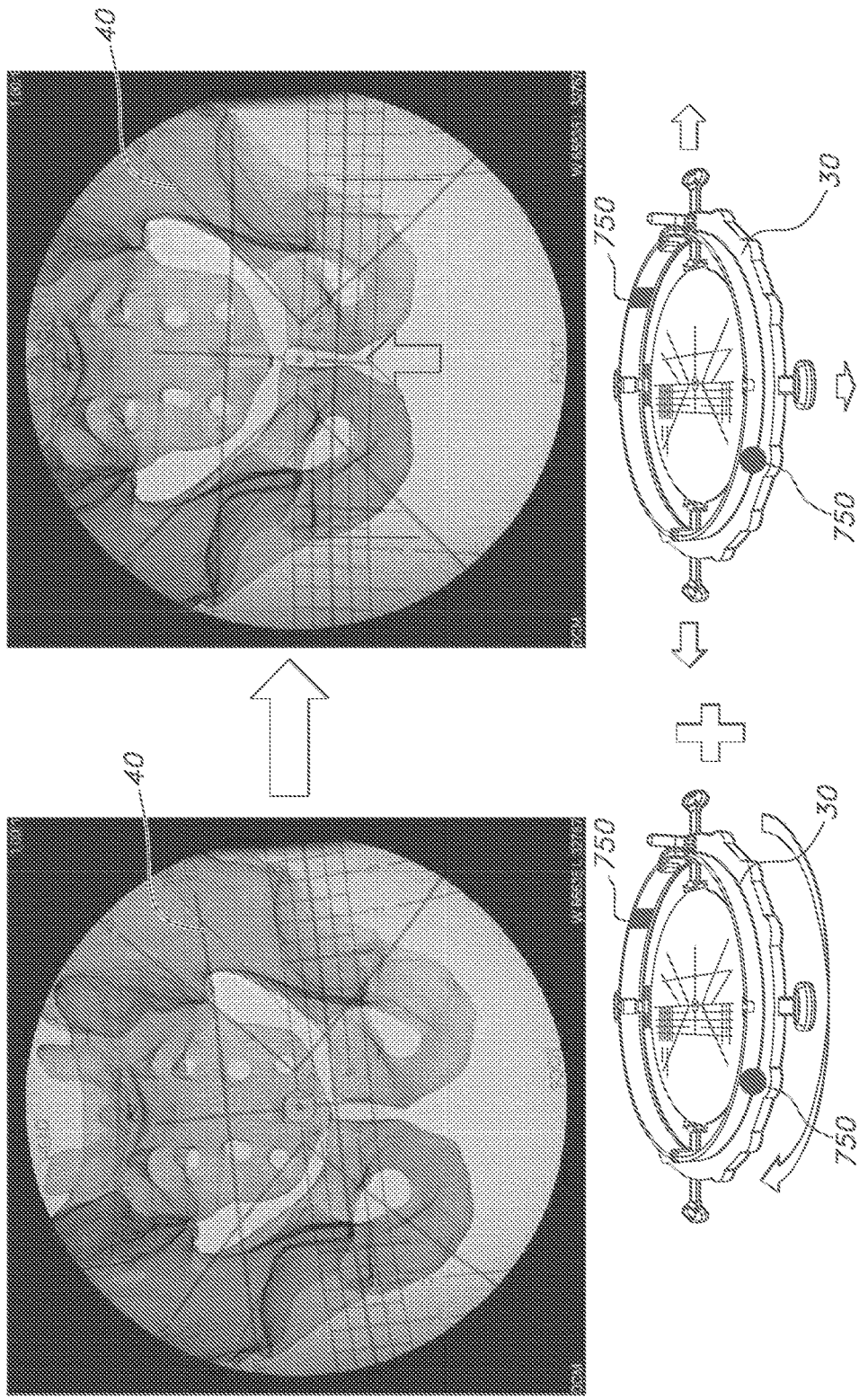
FIG. 7 is an illustrative embodiment of the displacement of the dimensioned pattern over the anatomy to quantify the rotation of the pelvis and thus the coronal plane of the patient.
Figure 8:
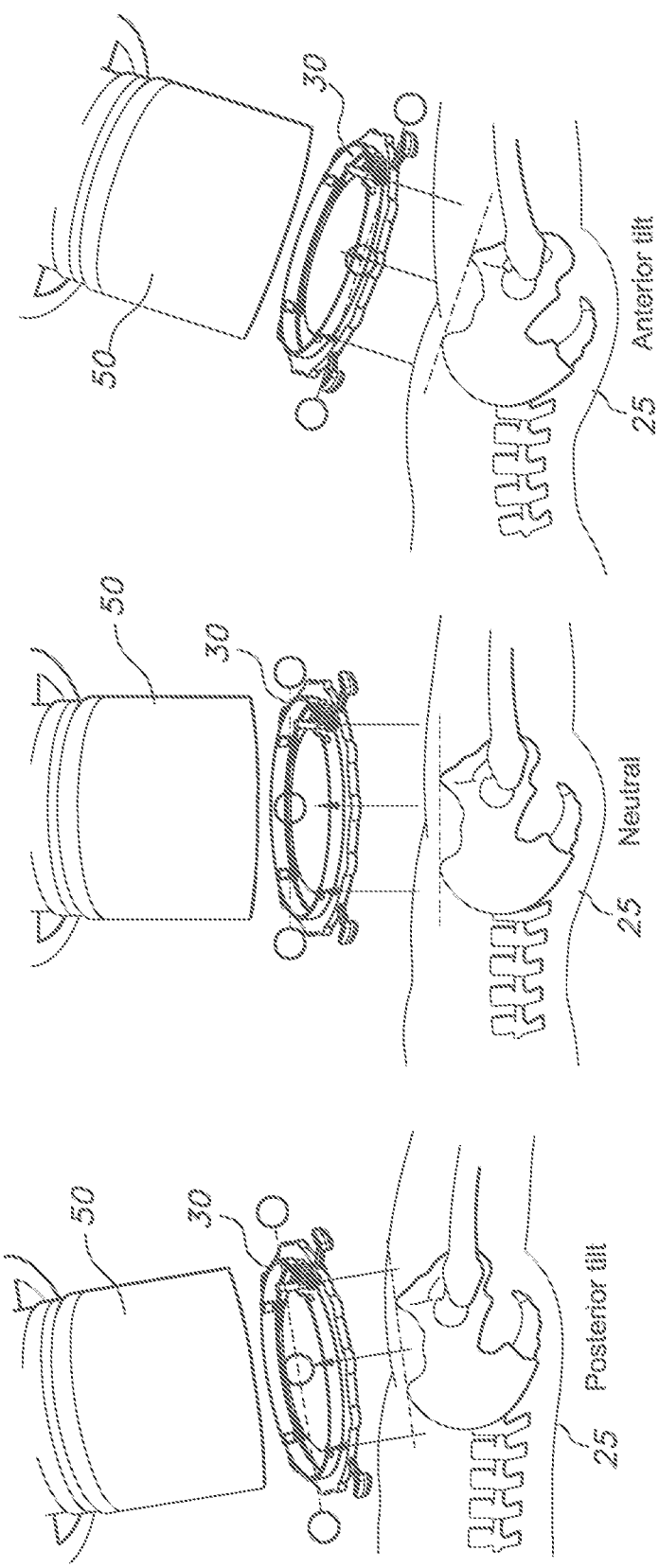
FIG. 8 is an illustrative embodiment of showing the effective transposition of the patient sagital reference plane onto the machine with the use of the dimensioned pattern device.
Figure 9:
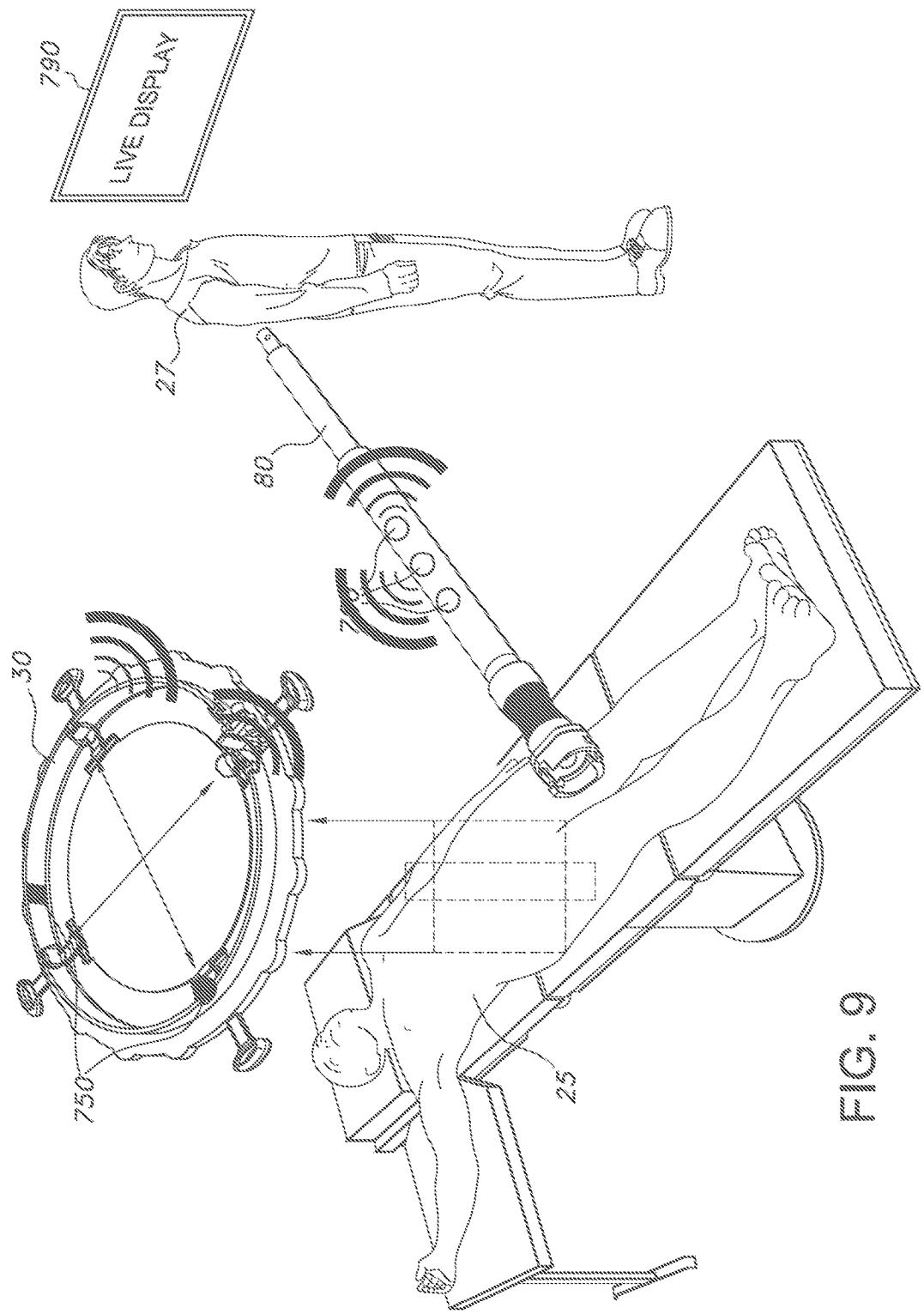
FIG. 9 is. a schematic diagram of showing the interaction of the alignment device and surgical instrument.

Now referring to FIGS. 7-9, an anatomical image, such as an X-ray image, of a patient 25 is acquired during a surgical procedure. Digital X-ray images are acquired intra-operatively, during surgical procedures such as joint replacements and trauma fracture reductions and deformity correction and implant placement/alignment. The acquired image can be viewed or further processed on a device, such as a computer with a monitor. A dimensioned radiopaque pattern 40 specific to the anatomical reference for a known surgical procedure is attached to a medical imaging device such as a fluoroscopic or portable radiographic machine. In another illustrative embodiment, the dimensioned pattern 40 is generated digitally on to the image. See U.S. Pat. Nos. 8,611,504, 9,456,874 and 9,610,134 hereby specifically incorporated by reference.

The intraoperative digital imaging allows immediate visualization of the bony anatomy of a patient 25. The skeleton's anatomical landmarks for reference is well documented in medical textbook and literature. Using the image produced by the imaging machine as a non-invasive source of anatomical data, the dimensioned radiopaque pattern 40, can be adjusted and used to align over pre-determined known anatomical landmarks. This allows a user to ensure and verify that the anatomical plane represented within the medical image is an accurate representation of the desired anatomical plane in the Z and Y axis.

The specifically spaced and quantified vertical elements of a dimensioned known pattern, are overlaid onto a AP Pelvis in the center of a 2D image. This allows a user 27 to adjust the imaging machine or the position of the patient 25 to adequately and accurately represent a patient specific rotated AP Pelvis view. This defines the coronal plane of the pelvis or the Z axis. The specifically spaced and quantified horizontal elements of a dimensioned pattern, overlaid on a AP Pelvis in the center of a 2D image, allows a user 27 to adjust the imagine machine or the patient position to adequately and accurately represent a patient specific tilt in the AP Pelvis image. This defines the sagittal plane of the pelvis or the y axis.

In one illustrative embodiment of a primary alignment device 30 is shown. In the primary alignment device 30, the analog tilt is made of an outer ring that rotates around a flat circular plane for initial zeroing of the degree ring off the trued C-Arm position. The next ring rotates freely inside the degree ring allowing it to be set to a desired degree and keep the instrument at the desired angle allowing the instrument to be accurately guided into a 3D position in conjunction with the dimensioned grid.

The step of extrapolating the third axis from the 2D anatomical reference plane is shown. Once two axes have been identified, the surface of the imaging device becomes the parallel transposition of these two axes into space. As a result, the remaining axis can be identified as perpendicular to both these axes. At this point, a 3-dimensional reference plane, aligned accurately with the anatomy, is determined.

Additionally, a plurality of reference plane axis trackers 750 are positioned on the primary alignment device 30. These reference trackers can include: a graphic marker tracker, (an angular device measures a tool angle to the C-Arm angle wirelessly to compare the two), an accelerometer, gyroscope and stereoscopic camera. The stereo Image uses a SIAM model to judge distances. These trackers can be built into the ring of the alignment device 30.

Additionally, a plurality of reference plane axis trackers 760 are positioned on the surgical device 80. More specifically, these can include: passive RFID markers that are used with an active reader to read a time pulse to test for distance and at least one graphic marker tracker. These sensors and trackers generate a signal that is received by the signal receiver 107 that is communicatively coupled to an at least one processor 112 of the computing system 100. These are averaged based on weight of accuracy and importance to reduce error. The user 27 is then able to know where he or she is in place and where he or she needs to move, based on previous studies of landmarks and templates.

The use of a plurality of reference plane axis trackers positioned both on the primary alignment device 30, secondary alignment device 800, and on the surgical device, such as an instrument 80, allows a user 27 to navigate, live, and position in space, a surgical instrument in either one or multiple plane. The step of providing positioning data to a user 27 is shown. The positioning data can be communicating to an outside display unit, either analog or digital, including but not limited to a computer monitor, mobile device or portable augmented or virtual reality or heads-up type display 790.

Now referring to FIG. 10, a secondary alignment guide device 800 is shown, which is configured to non-invasively navigate a surgical instrument in at least one plane. The secondary alignment guide device 800 is configured to allow a user 27, such as a surgeon, to obtain a three-dimensional reference to anatomy from a c-arm image by zeroing it off a dimensioned radiolucent pattern 40 after aligning with it, as a plane and adjusting the secondary alignment guide device 800 to the desired degree for guidance. In one exemplary embodiment, the dimensioned radiolucent pattern 40 is attached to the C arm of an imaging system 50.

The secondary alignment guide device 800 is attached to a surgical device, such as an instrument 80 by an attachment mechanism such as cable ties. A 6 or 9 axis motion fusion type accelerometer and gyrometer 802 calculates the current angle of the surgical device 80. The surgical device 80, such as a tool is placed against the primary alignment device 30 that has been properly planed. In operation, the user 27 pushes the zero button 803 to sync the plane of the primary alignment device 30 with the surgical device, such as an instrument 80. The user 27 then presses adjustment buttons 804 and observes the number on the display 805 until he has the desired angle off of the reference plane he wishes to keep the surgical device 80. When at the angle, the LED bubble guide 806 lights up green, or yellow or red depending on how many degrees off the angle is while displaying the current angle. This information is then fed to the wireless module 807 to send the data back to a computational model for integration into other devices While the invention has been described with reference to preferred and example embodiments, it will be understood by those skilled in the art that a variety of modifications, additions and deletions are within the scope of the invention, as defined by the following claims.

The invention claimed is:

1. A method for intra-operatively navigating a surgical device during a surgical procedure using radiographic imaging;

the method comprising the steps of:

overlaying a primary alignment device comprised of a grid having a plurality of dimensioned radiopaque patterns over an image of a patient's anatomy;

defining a coronal plane of the patient anatomy with reference to the dimensioned radiopaque patterns;

defining a sagittal plane of the patient's anatomy with reference to the dimensioned radiopaque patterns;

extrapolating a third axis from the coronal plane and the sagittal plane to form a 3-dimensional reference plane;

obtaining intraoperative positional data for a surgical device with reference to the 3-dimensional reference plane;

attaching a surgical device to a secondary alignment device, wherein the secondary alignment device is comprised of a guide to provide an angle between the surgical device and the secondary alignment device, and aligning the secondary alignment device with the primary alignment device with reference to the defined coronal plane of the patient's anatomy and the defined sagittal plane of the patient's anatomy;

communicating the intraoperative positioning data of the surgical device to a user; and intra-operatively navigating the surgical device with reference to the positioning data further comprising the step of attaching the primary alignment device to the C arm head of a radiographic imaging device further comprising the step moving the primary alignment device, where the primary alignment device is comprised of: a movable inner circular section having a radio-opaque grid pattern corresponding to anatomical landmarks related to a surgical procedure, a plurality of radial fixturing grips attached to the inner section, each of said radial fixturing grips being configured to allowed planer movement of the inner circular section; said inner circular section positioned within an outer rotatable ring wherein said outer rotatable ring further comprises a plurality of slots positioned to retain each of said radial fixturing grips.

2. The method of claim 1 wherein the intraoperative positional data for a surgical device is obtained from a plurality of reference plane axis trackers positioned on the surgical device.

3. The method of claim 1 wherein the intraoperative positional data for the surgical device is obtained from a plurality of reference plane axis trackers positioned on the primary alignment device.

4. The method of claim 1 wherein the intraoperative positional data for the surgical device is obtained by comparing the angle the angle between the reference plane axis trackers positioned on the primary alignment device and reference plane axis trackers positioned on the secondary alignment device.

5. The method of claim 1 wherein the procedure is selected from the group consisting of: joint replacements, spine, trauma fracture reductions, deformity correction, implant placement, and implant alignment.

* * * * *